United States Patent
Bianchi et al.

(10) Patent No.: US 9,328,109 B2
(45) Date of Patent: May 3, 2016

(54) PROCESS FOR THE PREPARATION OF BENZOHETERO [1, 3] DIAZOLE COMPOUNDS DISUBSTITUTED WITH HETEROARYL GROUPS

(71) Applicant: ENI S.p.A., Rome (IT)

(72) Inventors: Gabriele Bianchi, L'Aquila (IT); Riccardo Po', Novara (IT)

(73) Assignee: ENI S.p.A., Rome (IT)

( * ) Notice: Subject to any disclaimer, the term of this patent is extended or adjusted under 35 U.S.C. 154(b) by 0 days.

(21) Appl. No.: 14/759,328

(22) PCT Filed: Jan. 13, 2014

(86) PCT No.: PCT/IB2014/058222
§ 371 (c)(1),
(2) Date: Jul. 6, 2015

(87) PCT Pub. No.: WO2014/108873
PCT Pub. Date: Jul. 17, 2014

(65) Prior Publication Data
US 2015/0344470 A1    Dec. 3, 2015

(30) Foreign Application Priority Data
Jan. 14, 2013  (IT) .............................. MI2013A0038

(51) Int. Cl.
*C07D 417/14* (2006.01)
(52) U.S. Cl.
CPC .................... *C07D 417/14* (2013.01)
(58) Field of Classification Search
CPC .................................................. C07D 417/14
See application file for complete search history.

(56) References Cited

FOREIGN PATENT DOCUMENTS

WO    WO 2013/021315 A1    2/2013

OTHER PUBLICATIONS

Steinberger et al. Org. Lett. 2011, 13, 90-93.*
International Search Report and Written Opinion issued Apr. 3, 2014 in PCT/IB2014/058222.
Samuel C. Price, et al., "Fluorine Substituted Conjugated Polymer of Medium Band Gap Yields 7% Efficiency in Polymer-Fullerene Solar Cells" Journal of the American Chemical Society, XP002665448, vol. 133, 2011, pp. 4625-4631.
Simon Steinberger, et al., "A-D-A-D-A-Type Oligothiophenes for Vacuum-Deposited Organic Solar Cells" Organic Letters, XP002665447, vol. 13, No. 1, 2011, pp. 90-93.
Huaxing Zhou, et al., "Donor-Acceptor Polymers Incorporating Alkylated Dithienylbenzothiadiazole for Bulk Heterojunction Solar Cells: Pronounced Effect of Positioning Alkyl Chains" Macromolecules, XP008145880, vol. 43, 2010, pp. 811-820.
Ji-Cheng Li, et al., "Synthesis of a benzothiadiazole/thiophene-based oligomer for bulk heterojunction photovoltaic cells" Synthetic Metals, XP0025962474, vol. 159, 2009, pp. 201-208.
Jeum-Jong Kim, et al., "A polymer gel electrolyte to achieve ≥6% power conversion efficiency with a novel organic dye incorporating a low-band-gap chromophore" Journal of Materials Chemistry, XP002665445, vol. 18, 2008, pp. 5223-5229.

* cited by examiner

*Primary Examiner* — Matthew Coughlin
(74) *Attorney, Agent, or Firm* — Oblon, McClelland, Maier & Neustadt, L.L.P.

(57) ABSTRACT

Process for the preparation of a benzohetero-[1,3]diazole compound disubstituted with brominated heteroaryl groups which comprises reacting at least one dihalogenated benzohetero[1,3]diazole compound with at least one brominated heteroaryl compound. Said benzohetero[1,3]diazole compound disubstituted with brominated heteroaryl groups can be advantageously used in the synthesis of compounds useful in the construction of solar concentrators (LSCs—"Luminescent Solar Concentrators"). Furthermore, said benzohetero[1, 3]diazole compound disubstituted with brominated heteroaryl groups can be advantageously used in the synthesis of photoactive polymers useful in the construction of photovoltaic devices (or solar devices) such as, for example, photovoltaic cells (or solar cells), photovoltaic modules (or solar modules), on both rigid or flexible supports. Furthermore, said benzohetero[1,3]diazole compound disubstituted with brominated heteroaryl groups can be advantageously used as precursor of monomeric units in the synthesis of semiconductor polymers.

18 Claims, No Drawings

PROCESS FOR THE PREPARATION OF BENZOHETERO [1, 3] DIAZOLE COMPOUNDS DISUBSTITUTED WITH HETEROARYL GROUPS

The present invention relates to a process for the preparation of a benzohetero[1,3]diazole compound disubstituted with heteroaryl groups.

More specifically, the present invention relates to a process for the preparation of a benzohetero[1,3]diazole compound disubstituted with brominated heteroaryl groups which comprises reacting at least one dihalogenated benzohetero[1,3] diazole compound with at least one brominated heteroaryl compound.

Said benzohetero[1,3]diazole compound disubstituted with brominated heteroaryl groups can be advantageously used in the synthesis of compounds useful in the construction of solar concentrators (LSCs—"Luminescent Solar Concentrators"). Furthermore, said benzohetero[1,3]diazole compound disubstituted with brominated heteroaryl groups can be advantageously used in the synthesis of photoactive polymers useful in the construction of photovoltaic devices (or solar devices) such as, for example, photovoltaic cells (or solar cells), photovoltaic modules (or solar modules), on both rigid or flexible supports. Furthermore said benzohetero[1,3] diazole compound disubstituted with brominated heteroaryl groups can be advantageously used as precursor of monomeric units in the synthesis of semiconductor polymers.

It is known that neither polymer or silicon photovoltaic cells (or solar cells) are capable of efficiently exploiting all solar radiation. Their efficiency, in fact, is maximum only within a certain spectrum range which comprises a part of visible radiation and a part of infrared radiation.

Spectrum converter materials which capture solar radiation outside the optimal spectral range and convert it to effective radiation, can be used for enhancing the performance of photovoltaic cells (or solar cells). Luminescent solar concentrators can also be produced with these materials, which allow a further increase in the production of current in photovoltaic cells (or solar cells).

Said luminescent solar concentrators generally consist of large sheets of material transparent to solar radiation, in which fluorescent substances are dispersed, which act as spectrum converters. Due to the effect of the optical phenomenon of total reflection, the radiation emitted by the fluorescent molecules is "guided" towards the thin edges of the sheet where it is concentrated on photovoltaic cells or solar cells positioned therein. In this way, large surfaces of low-cost materials (photoluminescent sheets) can be used for concentrating the light on small surfaces of high-cost materials (photovoltaic cells or solar cells).

It is known that some benzothiadiazole materials, in particular 4,7-di-2-thienyl-2,1,3-benzothiadiazole (DTB), are fluorescent substances which can be used as spectrum converter materials in luminescent solar concentrators. Materials of this type are described in international patent application WO 2011/048458 in the name of the Applicant.

4,7-di-2-thienyl-2,1,3-benzothiadiazole (DTB) is also used for the synthesis of electron-donor polymers used in the construction of photovoltaic devices (or solar devices) such as photovoltaic cells (or solar cells) as described, for example, in "Organic Photovoltaics: Mechanism, Materials and Devices" (2005), Wiley Ed., Chapter 17.

4,7-di-2-thienyl-2,1,3-benzothiadiazole (DTB) is a compound of great interest, whose synthesis has been the subject of numerous research studies.

4,7-di-2-thienyl-2,1,3-benzothiadiazole (DTB) is generally prepared by means of a Stille reaction, by reacting 4,7-dibromo-2,1,3-benzothiadiazole and an excess of tri-n-butyl (thien-2-yl)stannane. Said reaction is generally carried out in the presence of catalysts containing palladium, at temperatures ranging from 60° C. to 145° C., in the presence of solvents such as, for example, toluene, xylene, 1,2-dimethoxyethane, tetrahydrofuran, dimethylsulfoxide, N,N-dimethylformamide, for a time ranging from 35 minutes to 18 hours. The yields normally range from 70% to 98%.

According to what is described by Kitamura et al. in "Chemistry of Material" (1996), Vol. 8, pages 570-578, for example, 4,7-di-2-thienyl-2,1,3-benzothiadiazole (DTB) can be prepared by reacting 4,7-dibromo-2,1,3-benzothiadiazole and tri-n-butyl(thien-2-yl)stannane, in the presence of tetrahydrofuran, at 66° C., for 3 hours. Bis(triphenylphosphine) palladium-(II)chloride[$PdCl_2(PPh_3)_2$] is used as catalyst, in a quantity equal to 2 moles per 100 moles of 4,7-dibromo-2,1, 3-benzothiadiazole. At the end of the reaction, the solvent is removed by evaporation at reduced pressure and the residue obtained is purified by elution on a silica gel chromatographic column using a mixture of methylene chloride/hexane (1/1 vol/vol) as eluent, obtaining 4,7-di-2-thienyl-2,1,3-benzothiadiazole (DTB) with a yield equal to 82%.

An analogous process is described by Kim et al. in "Journal of Material Chemistry" (2008), Vol. 18, pages 5223-5229, in which 4,7-di-2-thienyl-2,1,3-benzothiadiazole (DTB) can be prepared by reacting 4,7-dibromo-2,1,3-benzothiadiazole and tri-n-butyl(thien-2-yl)stannane, in the presence of tetrahydrofuran, at 66° C., for 3 hours. Bis(triphenylphosphine) palladium-(II)chloride[$PdCl_2(PPh_3)_2$] is used as catalyst. Also in this case, at the end of the reaction, the solvent is removed by evaporation at reduced pressure and the residue obtained is purified by elution on a silica gel chromatographic column using a mixture of methylene chloride/hexane (1/1 vol/vol) as eluent, obtaining 4,7-di-2-thienyl-2,1,3-benzothiadiazole (DTB) with a yield equal to 88%.

It is also known that 4,7-di-2-thienyl-2,1,3-benzothiadiazole (DTB) can be functionalized on the thiophene ring, for example by means of halogenation reactions, in order to be used for obtaining more complex structures such as, for example, low-gap oligomers and/or conjugated polymers which can be used in the construction of photovoltaic devices (or solar devices).

Lee Y.-S. et al., in "Synthetic Metals" (2009), Vol. 159, pages 201-208, for example, describe a process for the synthesis of an oligomer composed of three units: 2,1,3-benzothiazole (B), 3,4-ethylenedioxythiophene (EDOT) and 3-hexylthiophene (HT). Said process comprises various steps in which both tin compounds and boron compounds are used. Said oligomer can be used in the construction of bulk heterojunction photovoltaic cells.

Cao Y. et al., in "Macromolecules" (2009), Vol. 42, pages 4410-4415, describe donor polymers containing repetitive units consisting of benzothiadiazole and four thiophene rings. Said polymers are obtained by means of a synthesis process which comprises various steps in which tin compounds are used. Said polymers allow photovoltaic cells with an improved activity to be obtained.

Cheng Y.-S. et al., in "Chemical Reviews" (2009), Vol. 109, pages 5868-5923, describe synthesis processes of various conjugated polymers which can be used in the construction of organic solar cells, among which polymers containing benzothiadiazole and thiophene units. Said processes envisage the use of both tin compounds and boron compounds.

The above processes, however, can have various drawbacks. In particular, these processes require:
- numerous passages and consequently higher production costs and disposal costs of the waste products;
- the use of compounds such as, for example, tri-n-butyl (thien-2-yl)stannane, which create problems of toxicity, from both an environmental point of view and also with respect to the health of the operators, in addition to problems relating to their disposal which is often costly, with consequently higher production costs and disposal costs of the waste products;
- the use of compounds such as, for example, 2-thienylboronic acid whose synthesis requires the use of highly flammable and dangerous substances such as alkyl lithium compounds and completely anhydrous operating conditions;
- the use of relatively high quantities of catalyst: normally 2 moles of palladium per 100 moles of 4,7-dibromo-2,1,3-benzothiadiazole are used and, in any case, never less than 0.5 moles per 100 moles of dibromo-derivative (although the quantities, in absolute terms, are small, they are in any case high, considering the cost of palladium or, as it is not always possible to prepare its complexes in situ, of its complexes);
- in some cases, the use of solvents which can have problems of toxicity, from both an environmental point of view and also with respect to the health of the operators, in addition to problems relating to their disposal which is often costly.

Systems are also described in literature for forming aryl-aryl (Ar—Ar) bonds without the use of derivatives of tin.

Mori A. et al., for example, in "Organic Letters" (2005), Vol. 7(22), pages 5083-5085, describe a direct arylation reaction according to the following scheme:

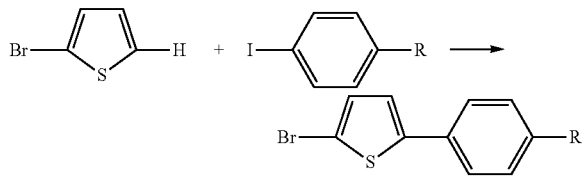

wherein R can be, for example, —OMe, —COOEt, —CN, —CF$_3$, in the presence of a catalyst containing palladium such as, for example, bis(triphenylphosphine)palladium(II) chloride[PdCl$_2$(PPh$_3$)$_2$], a solvent such as, for example, dimethylsulfoxide (DMSO) and a silver(I)-nitrate/potassium fluoride system (AgNO$_3$/KF) as activator, at a temperature ranging from 60° C. to 100° C., for 5 hours.

Even the above process, however, can have various drawbacks such as, for example:
- the use of the silver(I)nitrate/potassium fluoride system (AgNO$_3$/KF) as activator as silver (I) nitrate and potassium fluoride are toxic substances, from both an environmental point of view and also with respect to the health of the operators, and they are also corrosive;
- the use of iodinated aryl compounds which are relatively costly and have a low stability.

The Applicant has therefore considered the problem of finding a process for the preparation of a benzohetero[1,3]diazole compound disubstituted with brominated heteroaryl groups capable of overcoming the above drawbacks. In particular, the Applicant has considered the problem of finding a process for the preparation of a benzohetero[1,3]diazole compound disubstituted with brominated heteroaryl groups, through direct arylation, more specifically through a double direct arylation, of a dihalogenated benzohetero[1,3]diazole compound.

The Applicant has now found that the preparation of a benzohetero[1,3]diazole compound disubstituted with brominated heteroaryl groups can be carried out by means of a process comprising a double direct arylation of a dihalogenated benzohetero[1,3]diazole compound, more specifically, by means of a process which comprises reacting at least one dihalogenated benzohetero[1,3]diazole compound with at least one brominated heteroaryl compound.

There are numerous advantages obtained by operating according to the above process such as, for example:
- simpler synthesis and consequently lower production costs and disposal costs of the waste products;
- use of compounds which do not create problems of toxicity from both an environmental point of view and also with respect to the health of the operators, in addition to problems relating to their disposal which is often costly, with consequent lower production costs and disposal costs of the waste products;
- use of brominated or chlorinated aryl compounds which are more economical and more stable with respect to iodinated aryl compounds.

Said benzohetero[1,3]diazole compound disubstituted with brominated heteroaryl groups can be advantageously used in the synthesis of compounds that can be adopted in the construction of solar concentrators (LSCs "Luminescent Solar Concentrators"). Furthermore, said benzohetero[1,3]diazole compound disubstituted with brominated heteroaryl groups can be advantageously used in the synthesis of photoactive polymers which can be adopted in the construction of photovoltaic devices (or solar devices) such as, for example, photovoltaic cells (or solar cells), photovoltaic modules (or solar modules), on both a rigid and flexible support. Said benzohetero[1,3]diazole compound disubstituted with brominated heteroaryl groups can also be advantageously used as a precursor of monomeric units in the synthesis of semiconductor polymers.

An object of the present invention therefore relates to a process for the preparation of a benzohetero[1,3]diazole compound disubstituted with brominated heteroaryl groups having general formula (I):

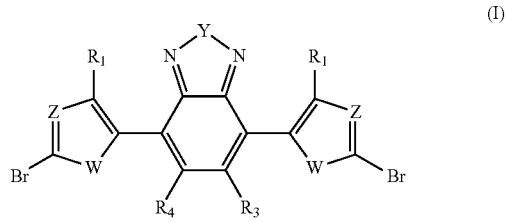

wherein:
- W represents an oxygen atom; a sulfur atom; an NR group wherein R represents a hydrogen atom, or a $C_1$-$C_{20}$, preferably $C_2$-$C_{10}$, alkyl group;
- Y represents a sulfur atom; an oxygen atom; a selenium atom; an NR group wherein R represents a hydrogen atom, or a linear or branched $C_1$-$C_{30}$, preferably $C_6$-$C_{24}$, alkyl group;
- Z represents a nitrogen atom; or a group CR$_2$ wherein R$_2$ represents a hydrogen atom, or a linear or branched $C_1$-$C_{20}$, preferably $C_2$-$C_{15}$, alkyl group;

$R_1$ represents a hydrogen atom; a linear or branched $C_1$-$C_{20}$, preferably $C_2$-$C_{10}$, alkyl group; a cycloalkyl group optionally substituted; an aryl group optionally substituted; a linear or branched $C_1$-$C_{20}$, preferably $C_2$-$C_{10}$, alkoxyl group; a polyethyleneoxyl group R—O—[—CH$_2$—CH$_2$—O]$_n$— wherein R has the same meaning defined above and n is an integer ranging from 1 to 4; a group —R'—OH wherein R' represents a linear or branched $C_1$-$C_{20}$, preferably $C_2$-$C_{10}$, alkylene group; a group —R'—OR" wherein R' has the same meanings defined above and R" represents a linear or branched $C_1$-$C_{20}$, preferably $C_2$-$C_{10}$, alkyl group, or a polyethyleneoxyl group R—O—[—CH$_2$—CH$_2$—O]$_n$— wherein R has the same meaning defined above and n is an integer ranging from 1 to 4; a group —COR wherein R has the same meanings defined above; a group —COOR wherein R has the same meanings defined above; a group —CHO; a cyano group (—CN);

or $R_1$ and $R_2$ can be optionally bound to each other so as to form, together with the carbon atoms to which they are bound, a cycle or a polycyclic system containing from 3 to 14 carbon atoms, preferably from 4 to 6 carbon atoms, saturated, unsaturated, or aromatic, optionally containing one or more heteroatoms such as, for example, oxygen, sulfur, nitrogen, silicon, phosphorous, selenium;

$R_3$ and $R_4$, the same as each other, represent a hydrogen atom; a linear or branched $C_1$-$C_{20}$, preferably $C_2$-$C_{10}$, alkyl group; a linear or branched $C_1$-$C_{20}$, preferably $C_2$-$C_{10}$, alkoxyl group; a group —COOR wherein R has the same meanings defined above; a cyano group (—CN);

or $R_3$ and $R_4$ can be optionally bound to each other so as to form, together with the carbon atoms to which they are bound, a cycle or a polycyclic system containing from 3 to 14 carbon atoms, preferably from 4 to 6 carbon atoms, saturated, unsaturated, or aromatic, optionally containing one or more heteroatoms such as, for example, oxygen, sulfur, nitrogen, silicon, phosphorous, selenium;

said process comprising reacting at least one dihalogenated benzohetero[1,3]diazole compound having general formula (II):

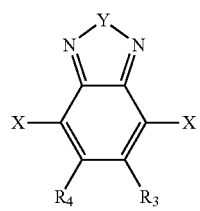

(II)

wherein X represents a halogen atom selected from chlorine, bromine, preferably bromine; Y, $R_3$ and $R_4$ have the same meanings described above;

with at least one brominated heteroaryl compound having general formula (III):

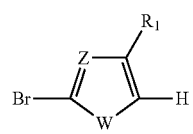

(III)

wherein W, Z and $R_1$, have the same meanings described above.

For the aim of the present description and of the following claims, the definitions of the numerical ranges always comprise the extremes unless otherwise specified.

The term "$C_1$-$C_{20}$ alkyl group" or "$C_1$-$C_{30}$ alkyl group" refers to a linear or branched alkyl group having from 1 to 20 carbon atoms or from 1 to 30 carbon atoms, respectively. Specific examples of a $C_1$-$C_{20}$ alkyl group or of a $C_1$-$C_{30}$ alkyl group are: methyl, ethyl, n-propyl, iso-propyl, n-butyl, iso-butyl, t-butyl, pentyl, ethyl-hexyl, hexyl, heptyl, octyl, nonyl, decyl, dodecyl.

The term "$C_1$-$C_{20}$ alkylene group" refers to a linear or branched alkylene group having from 1 to 20 carbon atoms. Specific examples of a $C_1$-$C_{20}$ alkylene group are: methylene, ethylene, n-propylene, iso-propylene, n-butylene, iso-butylene, t-butylene, pentylene, ethyl-hexylene, hexylene, heptylene, octylene, nonylene, decylene, dodecylene The term "cycloalkyl group" refers to a cycloalkyl group having from 3 to 10 carbon atoms. Said cycloalkyl group can be optionally substituted with one or more groups, equal to or different from each other, selected from: halogen atoms such as, for example, fluorine, chlorine, preferably fluorine; hydroxyl groups; $C_1$-$C_{20}$ alkyl groups; $C_1$-$C_{20}$ alkoxyl groups; cyano groups; amino groups; nitro groups. Specific examples of a cycloalkyl group are: cyclopropyl, 2,2-difluorocyclopropyl, cyclobutyl, cyclopentyl, cyclohexyl, methylcyclohexyl, methoxycyclohexyl, fluorocyclohexyl, phenylcyclohexyl.

The term "aryl group" refers to an aromatic carbocyclic group. Said aromatic carbocyclic group can be optionally substituted with one or more groups, equal to or different from each other, selected from: halogen atoms such as, for example, fluorine, chlorine, preferably fluorine; hydroxyl groups; $C_1$-$C_{20}$ alkyl groups; $C_1$-$C_{20}$ alkoxyl groups; cyano groups; amino groups; nitro groups. Specific examples of an aryl group are: phenyl, methylphenyl, trimethylphenyl, methoxyphenyl, hydroxyphenyl, phenyloxyphenyl, fluorophenyl, pentafluorophenyl, chlorophenyl, nitrophenyl, dimethylamminophenyl, naphthyl, phenylnaphthyl, phenanthrene, anthracene.

The term "$C_1$-$C_{20}$ alkoxyl group" refers to a linear or branched alkoxyl group having from 1 to 20 carbon atoms. Specific examples of a $C_1$-$C_{20}$ alkoxyl group are: methoxyl, ethoxyl, n-propoxyl, iso-propoxyl, n-butoxyl, iso-butoxyl, t-butoxyl, pentoxyl, hexyloxyl, heptyloxyl, octyloxyl, nonyloxyl, decyloxyl, dodecyloxyl.

The term "polyethyleneoxyl group" refers to a group having oxyethylene units in the molecule. Specific examples of a polyethyleneoxyl group are: methyloxy-ethyleneoxyl, methyloxy-diethyleneoxyl, 3-oxatetraoxyl, 3,6-dioxaheptyloxyl, 3,6,9-trioxadecyloxyl, 3,6,9,12-tetraoxahexadecyloxyl.

The term "cyclo or polycyclic system" refers to a system containing one or more rings containing from 3 to 14 carbon atoms, optionally containing heteroatoms selected from nitrogen, oxygen, sulfur, silicon, selenium, phosphorous. Specific examples of a cyclo or polycyclic system are: thieno[3,2-b]thiophene, thiadiazole, benzothiophene, quinoxaline, pyridine.

The above process can be carried out according to the following scheme:

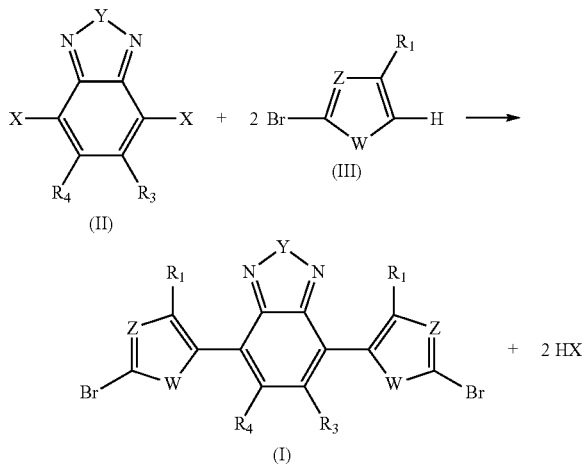

wherein X, Y, Z, W, $R_1$, $R_3$ and $R_4$, have the same meanings described above.

According to a preferred embodiment of the present invention, said dihalogenated benzohetero[1,3]diazole compound having general formula (II) and said brominated heteroaryl compound having general formula (III) can be used in molar ratios ranging from 1:2 to 1:20, preferably ranging from 1:4 to 1:12.

According to a further preferred embodiment of the present invention, said process relates to the preparation of a benzohetero[1,3]diazole compound disubstituted with brominated heteroaryl groups having general formula (I) wherein:

W represents a sulfur atom, or an oxygen atom, preferably a sulfur atom;

Y represents a sulfur atom, an oxygen atom, or an NR group wherein R represents a $C_1$-$C_{20}$ alkyl group, preferably a sulfur atom;

Z represents a nitrogen atom, or a group $CR_2$ wherein $R_2$ is a hydrogen atom, or it represents a $C_1$-$C_{20}$ alkyl group, preferably a group $CR_2$ wherein $R_2$ is a dodecyl;

$R_1$, $R_3$, and $R_4$, represent a hydrogen atom.

According to a particularly preferred embodiment of the present invention, said process relates to the preparation of 4,7-bis-(5-bromo-4-dodecyl-2-thienyl)-2,1,3-benzothiadiazole corresponding to a benzohetero-[1,3]diazole compound disubstituted with brominated heteroaryl groups having general formula (I) wherein W represents a sulfur atom, Y represents a sulfur atom, Z represents a group $CR_2$ wherein $R_2$ represents a dodecyl group and $R_1$, $R_3$, and $R_4$, represent a hydrogen atom, said process comprising reacting 4,7-dibromo-2,1,3-benzothiadiazole corresponding to a dihalogenated benzohetero[1,3]diazole compound having general formula (II) wherein X represents a bromine atom, Y represents a sulfur atom, and $R_3$ and $R_4$ represent a hydrogen atom, with a brominated thiophene corresponding to a brominated heteroaryl compound having general formula (III) wherein W represents a sulfur atom, Z represents a group $CR_2$ wherein $R_2$ represents a dodecyl group and $R_1$ represents a hydrogen atom.

According to a preferred embodiment of the present invention, said process can be carried out in the presence of at least one weak organic base.

According to a preferred embodiment of the present invention, said weak organic base can be selected, for example, from: carboxylates of alkaline metals (e.g., sodium, potassium, caesium) or alkaline-earth metals (e.g., magnesium, calcium) such as, for example, potassium acetate, sodium acetate, caesium acetate, magnesium acetate, calcium acetate, potassium propionate, sodium propionate, caesium propionate, magnesium propionate, calcium propionate, or mixtures thereof; carbonates of alkaline metals (e.g., lithium, sodium, potassium, caesium) or alkaline-earth metals (e.g., magnesium, calcium) such as, for example, lithium carbonate, potassium carbonate, sodium carbonate, caesium carbonate, magnesium carbonate, calcium carbonate, or mixtures thereof; bicarbonates of alkaline metals (e.g., lithium, sodium, potassium, caesium) or alkaline-earth metals (e.g., magnesium, calcium) such as, for example, lithium bicarbonate, potassium bicarbonate, sodium bicarbonate, caesium bicarbonate, magnesium bicarbonate, calcium bicarbonate, or mixtures thereof; or mixtures thereof. Said weak organic base is preferably potassium acetate.

According to a preferred embodiment of the present invention, said dihalogenated benzohetero[1,3]diazole compound having general formula (II) and said weak organic base can be used in molar ratios ranging from 1:2.2 to 1:20, preferably ranging from 1:2.5 to 1:4.

According to a preferred embodiment of the present invention, said process can be carried out in the presence of at least one catalyst containing palladium.

According to a preferred embodiment of the present invention, said catalyst containing palladium can be selected from: palladium compounds in oxidation state (0) or (II) such as, for example: palladium(II)chloride[$PdCl_2$], palladium(II)acetate [$Pd(OAc)_2$], bis(dibenzylidene)palladium(0) [$Pd(dba)_2$ wherein dba=$C_6H_5CH$=$CHCOCH$=$CHC_6H_5$], bis(acetonitrile)palladium(II)chloride[$Pd(CH_3CN)_2Cl_2$], or mixtures thereof. Said catalyst containing palladium is preferably palladium(II)acetate[$Pd(OAc)_2$].

According to a preferred embodiment of the present invention, said dihalogenated benzohetero[1,3]diazole compound having general formula (II) and said catalyst containing palladium can be used in molar ratios ranging from 100:0.1 to 100:3, preferably ranging from 100:0.4 to 100:2.

According to a preferred embodiment of the present invention, said dihalogenated benzohetero[1,3]diazole compound having general formula (II) can be used at a molar concentration ranging from 0.05 M to 2 M, preferably ranging from 0.1 M to 1.5 M.

According to a preferred embodiment of the present invention, said process can be carried out in the presence of at least one dipolar aprotic organic solvent.

According to a preferred embodiment of the present invention, said dipolar aprotic organic solvent can be selected, for example, from: N,N-dimethylacetamide (DMAc), dimethylsulfoxide (DMSO), N-methylpyrrolidone (NMP), dimethylformamide (DMF), or mixtures thereof. Said dipolar aprotic organic solvent is preferably N,N-dimethylacetamide (DMAc).

According to a preferred embodiment of the present invention, said dihalogenated benzohetero[1,3]diazole compound having general formula (II) can be used in said dipolar aprotic organic solvent in such a quantity so as to have a molar concentration in said solvent ranging from 0.05 M to 0.5 M, preferably ranging from 0.08 M to 0.2 M.

According to a preferred embodiment of the present invention, said process can be carried out at a temperature ranging from 80° C. to 170° C., preferably ranging from 100° C. to 150° C.

According to a preferred embodiment of the present invention, said process can be carried out for a time ranging from 30 minutes to 36 hours, preferably ranging from 1 hour to 30 hours.

The dihalogenated benzohetero[1,3]diazole compound having general formula (II) can be obtained according to processes known in the art, for example, by halogenation of the corresponding benzohetero-[1,3]diazole compounds. Further details relating to said processes can be found, for example, in international patent application WO 2007/081991, or in "Journal of Heterocyclic Chemistry" (1970), Vol. 7, Issue 3, pages 629-633, in the article of Pilgram et al.

The brominated heteroaryl compound having general formula (III) can be easily found on the market.

Some illustrative and non-limiting examples are provided for a better understanding of the present invention and for its practical embodiment.

EXAMPLE 1

Preparation of 4,7-bis-(5-bromo-4-dodecyl-2-thienyl)-2,1,3-benzothiadiazole having formula (a)

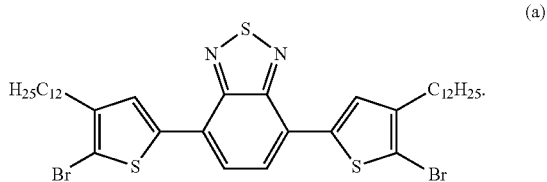

(a)

4,7-dibromo-2,1,3-benzothiadiazole (0.294 g, 1.0 mmoles), potassium acetate (0.295 g, 3.0 mmoles), N,N-dimethylacetamide (DMAc) (5 ml), 2-bromo-3-dodecyl-thiophene (0.994 g, 3.0 mmoles) and palladium(II)acetate[Pd(OAc)$_2$] (1.2 mg, 0.005 mmoles), were charged into a 10 ml Pyrex glass reactor equipped with a screw stopper.

The reactor was placed in an oil bath preheated to 130° C. and left under vigorous stirring for 24 hours. After cooling to room temperature (25° C.), the reaction mixture was introduced into a saturated solution of sodium chloride (25 ml) and extracted with ethyl acetate (3×25 ml). The organic phase obtained was dried on anhydrous sodium sulfate and evaporated. The residue obtained (brown solid) was purified by flash chromatography on silica gel using n-heptane as eluent, obtaining 124 mg of pure 4,7-bis-(5-bromo-4-dodecyl-2-thienyl)-2,1,3-benzothiadiazole having formula (a) as a red solid (yield 23%).

Said 4,7-bis-(5-bromo-4-dodecyl-2-thienyl)-2,1,3-benzothiadiazole was characterized by means of $^1$H-NMR (400 MHz, CDCl$_3$) obtaining the following spectrum: δ=7.76 (s, 2H), 7.73 (s, 2H), 2.65-2.61 (m, 4H), 1.69-1.65 (m, 4H), 1.38-1.36 (m, 8H), 1.26-1.24 (m, 28H), 0.89-0.85 (m, 6H).

Said 4,7-bis-(5-bromo-4-dodecyl-2-thienyl)-2,1,3-benzothiadiazole was also characterized by means of MS mass analysis obtaining the following value: m/z: 795.36 [MH]$^+$.

The invention claimed is:

1. A process for the preparation of a benzo-hetero[1,3]diazole compound disubstituted with brominated heteroaryl groups having general formula (I):

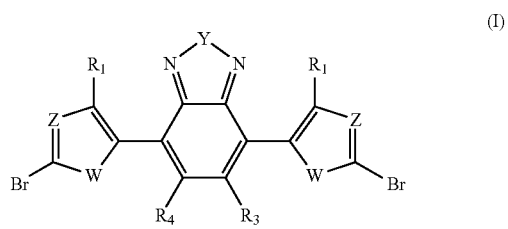

(I)

wherein:
W represents an oxygen atom; a sulfur atom; an NR group wherein R represents a hydrogen atom, or a $C_1$-$C_{20}$ alkyl group;
Y represents a sulfur atom; an oxygen atom; a selenium atom; an NR group wherein R represents a hydrogen atom, or a linear or branched $C_1$-$C_{30}$ alkyl group;
Z represents a nitrogen atom; or a group CR$_2$ wherein R$_2$ represents a hydrogen atom, or a linear or branched $C_1$-$C_{20}$ alkyl group;
R$_1$ represents a hydrogen atom; a linear or branched $C_1$-$C_{20}$ alkyl group; a cycloalkyl group optionally substituted; an aryl group optionally substituted; a linear or branched $C_1$-$C_{20}$ alkoxyl group; a polyethyleneoxyl group R—O—[—CH$_2$—CH$_2$—O]$_n$— wherein R represents a hydrogen atom, or a $C_1$-$C_{20}$ alkyl group and n is an integer ranging from 1 to 4; a group —R'—OH wherein R' represents a linear or branched $C_1$-$C_{20}$ alkylene group; a group —R'—OR" wherein R' has the same meanings defined above and R" represents a linear or branched $C_1$-$C_{20}$ alkyl group, or a polyethyleneoxyl group R—O—[—CH$_2$—CH$_2$—O]$_n$— wherein R represents a hydrogen atom, or a $C_1$-$C_{20}$ alkyl group and n is an integer ranging from 1 to 4; a group —COR wherein R represents a hydrogen atom, or a $C_1$-$C_{20}$ alkyl group; a group —COOR wherein R represents a hydrogen atom, or a $C_1$-$C_{20}$ alkyl group; a group —CHO; a cyano group (—CN);
or R$_1$ and R$_2$ can be optionally bound to each other so as to form, together with the carbon atoms to which they are bound, a cycle or a polycyclic system containing from 3 to 14 carbon atoms, saturated, unsaturated, or aromatic, optionally containing one or more heteroatoms;
R$_3$ and R$_4$, the same as each other, represent a hydrogen atom; a linear or branched $C_1$-$C_{20}$ alkyl group; a linear or branched $C_1$-$C_{20}$ alkoxyl group; a group —COOR wherein R represents a hydrogen atom, or a $C_1$-$C_{20}$ alkyl group; a cyano group (—CN);
or R$_3$ and R$_4$ can be optionally bound to each other so as to form, together with the carbon atoms to which they are bound, a cycle or a polycyclic system containing from 3 to 14 carbon atoms, saturated, unsaturated, or aromatic, optionally containing one or more heteroatoms; said process comprising reacting at least one dihalogenated benzohetero[1,3]diazole compound having general formula (II):

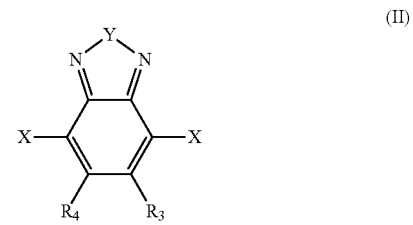

(II)

wherein X represents a halogen atom selected from chlorine, bromine; Y, $R_3$ and $R_4$ have the same meanings described above; with at least one brominated heteroaryl compound having general formula (III):

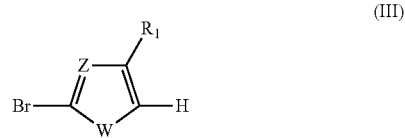

wherein W, Z and $R_1$, have the same meanings described above.

2. The process according to claim 1, wherein said dihalogenated benzohetero[1,3]diazole compound having general formula (II) and said brominated heteroaryl compound having general formula (III) are used in molar ratios ranging from 1:2 to 1:20.

3. The process according to claim 1, wherein said process relates to the preparation of a benzohetero[1,3]diazole compound disubstituted with brominated heteroaryl groups having general formula (I) wherein:
W represents a sulfur atom, or an oxygen atom;
Y represents a sulfur atom, an oxygen atom, or an NR group wherein R represents a $C_1$-$C_{20}$ alkyl group;
Z represents a nitrogen atom, or a group $CR_2$ wherein $R_2$ is a hydrogen atom, or it represents a $C_1$-$C_{20}$ alkyl group;
$R_1$, $R_3$, and $R_4$, represent a hydrogen atom.

4. The process according to claim 1, wherein said process relates to the preparation of 4,7-bis-(5-bromo-4-dodecyl-2-thienyl)-2,1,3-benzothiadiazole corresponding to a benzohetero[1,3]diazole compound disubstituted with brominated heteroaryl groups having general formula (I) wherein W represents a sulfur atom, Y represents a sulfur atom, Z represents a group $CR_2$ wherein $R_2$ represents a dodecyl group and $R_1$, $R_3$, and $R_4$, represent a hydrogen atom, said process comprising reacting 4,7-di-bromo-2,1,3-benzothiadiazole corresponding to a dihalogenated benzohetero[1,3]diazole compound having general formula (II) wherein X represents a bromine atom, Y represents a sulfur atom, and $R_3$ and $R_4$ represent a hydrogen atom, with a brominated thiophene corresponding to a brominated heteroaryl compound having general formula (III) wherein W represents a sulfur atom, Z represents a group $CR_2$ wherein $R_2$ represents a dodecyl group and $R_1$ represents a hydrogen atom.

5. The process according to claim 1, wherein said process is carried out in the presence of at least one weak organic base.

6. The process according to claim 5, wherein said weak organic base is selected from carboxylates of alkaline or alkaline-earth metals; carbonates of alkaline or alkaline-earth metals; bicarbonates of alkaline or alkaline-earth metals; or mixtures thereof.

7. The process according to claim 5, wherein said dihalogenated benzohetero-[1,3]diazole compound having general formula (II) and said weak organic base are used in molar ratios ranging from 1:2.2 to 1:20.

8. The process according to claim 1, wherein said process is carried out in the presence of at least one catalyst containing palladium.

9. The process according to claim 8, wherein said catalyst containing palladium is selected from: compounds of palladium in oxidation state (0) or (II).

10. The process according to claim 8, wherein said dihalogenated benzohetero-[1,3]diazole compound having general formula (II) and said catalyst containing palladium are used in molar ratios ranging from 100:0.1 to 100:3.

11. The process according to claim 1, wherein said dihalogenated benzo-hetero[1,3]diazole compound having general formula (II) is used at a molar concentration ranging from 0.05 M to 2 M.

12. The process according to claim 1, wherein said process is carried out in the presence of at least one dipolar aprotic organic solvent.

13. The process according to claim 12, wherein said dipolar aprotic organic solvent is selected from N,N-dimethylacetamide (DMAc), dimethylsulfoxide (DMSO), N-methylpyrrolidone (NMP), N,N-dimethylformamide (DMF), or mixtures thereof.

14. The process according to claim 12, wherein said dihalogenated benzohetero-[1,3]diazole compound having general formula (II) is used in said dipolar aprotic organic solvent in such a quantity so as to have a molar concentration in said solvent ranging from 0.05 M to 0.5 M.

15. The process according to claim 1, wherein said process is carried out at a temperature ranging from 80° C. to 170° C.

16. The process according to claim 1, wherein said process is carried out for a time ranging from 30 minutes to 36 hours.

17. The process according to claim 6, wherein said carboxylates of alkaline or alkaline-earth metals are selected from potassium acetate, sodium acetate, cesium acetate, magnesium acetate, calcium acetate, potassium propionate, sodium propionate, cesium propionate, magnesium propionate, calcium propionate, or mixtures thereof; said carbonates of alkaline or alkaline-earth metals are selected from lithium carbonate, potassium carbonate, sodium carbonate, cesium carbonate, magnesium carbonate, calcium carbonate, or mixtures thereof; or said bicarbonates of alkaline or alkaline-earth metals are selected from lithium bicarbonate, potassium bicarbonate, sodium bicarbonate, cesium bicarbonate, magnesium bicarbonate, calcium bicarbonate, or mixtures thereof.

18. The process according to claim 9, wherein said compounds of palladium in oxidation state (0) or (II) are selected from palladium(II)chloride[$PdCl_2$], palladium(II)acetate[$Pd(OAc)_2$], bis(dibenzylidene)palladium(0) [$Pd_2(dba)_2$ where dba=$C_6H_5CH$=$CHCOCH$=$CHC_6H_5$], bis(acetonitrile)palladium(II)chloride[$Pd(CH_3CN)_2Cl_2$], or mixtures thereof.

* * * * *